United States Patent
Boyle (10) Patent No.: US 10,626,127 B1
(45) Date of Patent: Apr. 21, 2020

(54) THALLIUM SALEN FLUORESCENT TRACERS

(71) Applicant: National Technology & Engineering Solutions of Sandia, LLC, Albuquerque, NM (US)

(72) Inventor: Timothy J. Boyle, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 181 days.

(21) Appl. No.: 15/941,848

(22) Filed: Mar. 30, 2018

Related U.S. Application Data (63) Continuation-in-part of application No. 15/937,650, filed on Mar. 27, 2018, which is a continuation-in-part of application No. 14/488,989, filed on Sep. 17, 2014, now Pat. No. 10,106,727.

(60) Provisional application No. 62/477,330, filed on Mar. 27, 2017.

(51) Int. Cl.
  *C09K 11/06* (2006.01)
  *E21B 47/10* (2012.01)
  *C07F 5/00* (2006.01)

(52) U.S. Cl.
  CPC .............. *C07F 5/003* (2013.01); *C09K 11/06* (2013.01); *E21B 47/1015* (2013.01); *C09K 2211/1007* (2013.01); *C09K 2211/188* (2013.01)

(58) Field of Classification Search
  None
  See application file for complete search history.

(56) References Cited

U.S. PATENT DOCUMENTS 7,105,703 B1 * 9/2006 Atwood ............... B01J 31/1805
                                                              502/167

OTHER PUBLICATIONS

Wright et al, Synthesis and Reactivity of Dimeric Ar'TlTlAr' and Trimeric (Ar' 'Tl)3 (Ar', Ar" = Bulky Terphenyl Group) Thallium(I) Derivatives: Tl(I)-Tl(I) Bonding in Species Ligated by Monodentate Ligands, J.Am. Chem. Soc. 2005, 127, 13, 4794-4799 (Year: 2005).*

Boyle, T. J. et al., "Synthesis and Characterization of Structurally Diverse Alkaline-Earth Salen Compounds for Subterranean Fluid Flow Tracking", Inorganic Chemistry, 2018, pp. 2402-2415, vol. 57.

Dai, Z. et al., "Metalated Porous Porphyrin Polymers as Efficient Heterogeneous Catalysts for Cycloaddition of Epoxides with CO2 under Ambient Conditions", Journal of Catalysis, 2016, pp. 202-209, vol. 338.

(Continued)

*Primary Examiner* — Jeffrey D Washville
(74) *Attorney, Agent, or Firm* — Kevin W. Bieg (57) ABSTRACT

Thallium salens can be synthesized by reacting thallium alkoxide with a salen ligand. As examples of the invention, the dinuclear complexes $Tl_2$-(salo-$Bu^t$) and $Tl_2$-(saloPh-$Bu^t$) were synthesized by the reaction of thallium ethoxide with ($H_2$-salo-$Bu^t$) or ($H_2$-saloPh-$Bu^t$). These thallium salens may have applications as fluorescent tracers (or taggants) for subterranean fluid flows.

9 Claims, 12 Drawing Sheets

(56) References Cited

OTHER PUBLICATIONS

Meng, Q.-Y. et al., "Effect of Supercritical CO2 on the Copolymerization Behavior of Cyclohexene Oxide/CO2 and Copolymer Properties with DMC/Salen-Co(III) Catalyst System", Journal of Polymer Science, Part A: Polymer Chemistry, 2016, pp. 2785-2793, vol. 54.

Rakhtshah, J. et al., "Synthesis, Characterization and Heterogeneous Catalytic Application of a Nickel(II) Schiff Base Complex Immobilized on MWCNTs for the Hantzsch Four-component Condensation", Journal of Coordination Chemistry, 2017, pp. 340-360, vol. 70.

Rezaeifard, A. et al., "Enhanced Aqueous Oxidation Activity and Durability of Simple Manganese(III) Salen Complex Axially Anchored to Maghemite Nanoparticles", RSC Advances, 2016, pp. 64640-64650, vol. 6.

Sohn, C. et al., "Novel Aluminum—BODIPY Dyads: Intriguing Dual-Emission via Photoinduced Energy Transfer", Dalton Transactions, 2016, pp. 5825-5832, vol. 45.

Clarke, R. and Storr, T., "The Chemistry and Applications of Multimetallic Salen Complexes", Dalton Transactions, 2014, pp. 9380-9391, vol. 43.

Musa, M. A. et al., "Synthesis and Antimicrobial Activity of N,N'-Bis(2-hydroxylbenzyl)-1,2-ethanediamine Derivatives", Lett Drug Des Discov., 2010, pp. 165-170, vol. 7.

Atwood, D.A. and Harvey, M.J., "Group 13 Compounds Incorporating Salen Ligands", 2001, Chemical Reviews, pp. 37-52, vol. 101.

Cozzi, P.G. et al., "Metal-Salen Schiff Base Complexes in Catalysis: Practical Aspects", 2004, Chemical Society Review, pp. 410-421, vol. 33.

Dagorne, S. et al., "Gallium and Indium Complexes for Ring-Opening Polymerization of Cyclic Ethers, Esters and Carbonates", Coordination Chemistry Reviews, 2013, pp. 1869-1886, vol. 257.

Specklin, D. et al., "Mononuclear Salen-Gallium Complexes for Iso-Selective Ring-Opening Polymerization (ROP) of Rac-Lactide", Dalton Transactions, 2017, pp. 12824-12834, vol. 46.

Boyle, T.J. et al., "Synthesis and Characterization of Thallium-Salen Derivatives for Use as Underground Fluid Flow Tracers", Dalton Transactions, 2018, pp. 4162-4174, vol. 47.

\* cited by examiner

THALLIUM SALEN FLUORESCENT TRACERS

CROSS-REFERENCE TO RELATED APPLICATIONS

This application is a Continuation-in-Part of U.S. patent application Ser. No. 15/937,650, filed Mar. 27, 2018, which claims the benefit of U.S. Provisional Application No. 62/477,330, filed Mar. 27, 2017, and is a Continuation-in-Part of U.S. patent application Ser. No. 14/488,989, filed Sep. 17, 2014, all of which are incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to tracers to map deep underground fluid flows and, in particular, to thallium salen fluorescent tracers.

BACKGROUND OF THE INVENTION

Methods to understand and map underground deep fluid (water or oil) flows employ a wide range of technologies; however, the most successful approaches utilize a tracer (or taggant) that is selectively placed deep within the well and detected at the well-head upon elution. See U.S. Pat. No. 3,002,091 to F. E. Armstrong; U.S. Pat. No. 4,264,329 to J. R. Beckett; U.S. Pat. No. 4,742,873 to F. F. Craig; U.S. Pat. No. 3,993,131 to E. F. Reiedel; and S. K. Ritter, C&E News 92, 31 (2014). While taggant methods are useful, they suffer from a variety of limitations, with the biggest concerns being the relatively short (2-3 mo.) time of use and the limited number of unique taggants available.

Hydrocarbon-soluble compounds are being developed that can be intercalated into porous proppants and then sealed in with a polymeric coating. After placing the proppants in the appropriate underground locations during the drilling process, these soluble taggants, over time, gradually diffuse through the polymeric coating and are released into the bulk underground reservoir. Ideally, the soluble molecules are transported to the well-head, where routine sampling using simple analytical tools would be used to identify them. While the proppant coating will be used to control the time of release, the tracer molecules themselves must fulfill a variety of criteria, including being soluble in the various underground fluids of interest, surviving high temperature and pressures, be uniquely identifiable in trace quantities, and number in the 50-100+ range. Therefore, a series of salen-metal complexes have been explored due to their reported stability to high temperatures and pressures. (salen is a contraction for salicylaldehyde and ethylenediamine. $H_2$-salen is made by the condensation of salicylaldehyde and ethylenediamine). See T. J. Boyle et al., Inorg. Chem. 57(5), 2402 (2018); Z. F. Dai et al., J. Cat. 338, 202 (2016); Q. Y. Meng et al., J. Poly. Sci. A—Poly Chem. 54, 2785 (2016); J. Rakhtshah et al., J. Coord. Chem. 70, 340 (2017); A. Rezaeifard et al., Rsc Advances 6, 64640 (2016); and C. Sohn et al., Dalton Trans. 45, 5825 (2016). Further, modification to the electron rich rings of the salen ligands allows for tuning of the salen-metal complexes' solubility and identifying vibrational spectroscopic signature. When these modified ligands are combined with different metals, a nearly unlimited number of easily distinguishable taggants can be produced that should survive the underground environment of interest.

Numerous group 13 salen compounds have been structurally identified (>110 structures) and used for a variety of applications, including ceramic materials, light emitting diodes, antimicrobial agents, and polymerization catalyst; however, none have been applied to down-hole fluid flow tracking. See R. M. Clarke and T. Storr, Dalton Trans., 9365 (July, 2014); F. S. Nworie et al., J. Bas. Appl. Res. 2, 295 (2016); M. A. Musa et al., Lett. Drug Desg. Disc. 7, 165 (2010); D. A. Atwood and M. J. Harvey, Chem. Rev. 101, 37 (2001); P. G. Cozzi, Chem. Soc. Rev. 33, 410 (2004); S. Dagorne et al., Coord. Chem. Rev. 257, 1869 (2013); and D. Specklin et al., Dalton Trans. 46, 12824 (2017). However, no structure reports concerning Tl-salen derivatives have been published. While there are a number of M(I)-salen structures available, most of these are heterometallic derivatives forming alkali metal, silver, chromium or copper salts, or unusual oxo derivatives employing the alkali metals (A=Li, Na, K). See S. C. Ball et al., J. Chem. Soc.—Chem. Commun., 2147 (1995); I. Correia et al., Eur. J. Inorg. Chem., 732 (2005); G. B. Deacon et al., Inorg. Chim. Acta 360, 1364 (2007); R. Jia et al., Aust. J. Chem. 69, 20 (2016); and E. Solari et al., J. Chem. Soc., Dalton Trans., 2471 (1991). Cyclooctadiene rhodium(I) salen is the only homometallic M(I)-salen complex reported, where two Rh cations bind to different O and N atoms of the salen backbone. See C. Janiak et al., Dalton Trans., 3698 (2009). Note: a Rh(I)-salen derivative is also reported but the metal does not interact with the O or N atom of the salen but rather with a phosphino/thio moiety located off of the cyclohexyl salen backbone. See M. S. I. Masar et al., J. Am. Chem. Soc. 129, 10149 (2007).

Therefore, a need remains for structurally characterized salen derivatives for the heaviest congener, thallium.

SUMMARY OF THE INVENTION

The present invention is directed to a method to synthesize a thallium salen according to the reaction:

where Tl(OR*) is a thallium alkoxide, $H_2$-saloR'—R is a salen ligand, and $Tl_2$(saloR'—R) is the thallium salen. R is a substituent on a salen ring that can be, for example, a hydrocarbon, nitrate, sulfate, or alkoxide. R' is the linkage in the salen that can be, for example, an alkyl, phenyl, cyclohexyl, or hydrogen. As examples of the invention, thallium ethoxide was reacted with N,N'-bis(3,5-di-t-butylsalicylidene)-ethylenediamine ($H_2$-salo-Bu$^r$) or N,N'-bis(3,5-di-t-butylsalicylidene)-1,2-phenylenediamine ($H_2$-saloPh-Bu$^r$) to form [((μ-O)$_{2,K}$¹—(N)(N')salo-Bu$^r$)Tl$_2$] or {[((μ-O)$_2$saloPh-Bu$^r$)Tl$_2$][((μ-O)$_{2,K}$¹—(N)(N')saloPh-Bu$^r$)Tl$_2$]}. The exemplary thallium salen derivatives were characterized for potential use as monitors (or taggants) or as models for Group 13 complexes for subterranean fluid flows.

BRIEF DESCRIPTION OF THE DRAWINGS

The detailed description will refer to the following drawings, wherein like elements are referred to by like numbers.

DETAILED DESCRIPTION OF THE INVENTION

The present invention is directed to the synthesis and characterization of thallium salen fluorescent tracers. The general reaction for these compounds is shown in eq 1.

$$2[Tl(OR^*)] + H_2\text{-saloR'—R} \rightarrow [Tl_2(\text{saloR'—R})] + 2HOR^* \quad (1)$$

where Tl(OR*) is a thallium alkoxide and H$_2$-saloR'—R is a salen ligand. R is a substituent on the salen ring and can be a wide variety of functional groups, including, but not limited to, hydrocarbons, nitrates, sulfates, alkoxides (methoxide), etc. R' is the linkage in the salen and can be an alkyl, phenyl, cyclohexyl, or hydrogen, for example.

As examples of the invention, the coordination behavior of Tl(I) with two salen ligands is described below. These exemplary thallium salens were synthesized according to the reaction:

$$2[Tl(OEt)] + H_2\text{-saloR'—Bu}^t \rightarrow [Tl_2(\text{saloR'—Bu}^t)] + 2HOEt \quad (2)$$

where R'=CH$_2$CH$_2$ or C$_6$H$_4$.

Figure 1A:
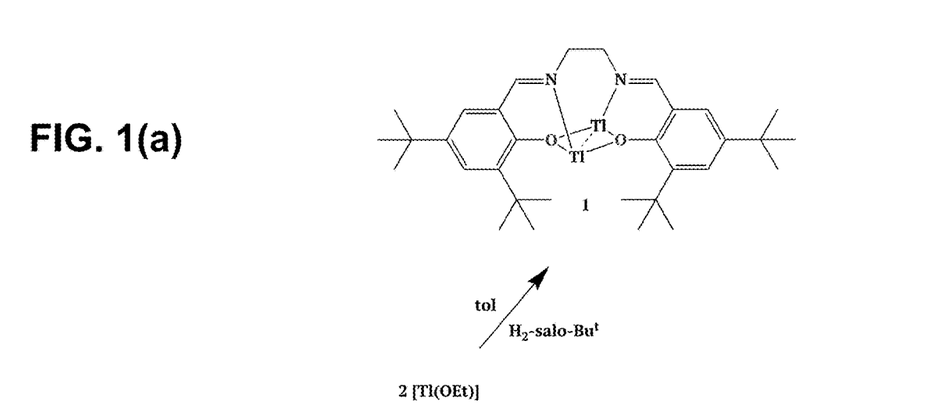
FIGS. 1(a) and 1(b) are schematic representations of the synthesis of compounds 1 and 2, respectively.
Figure 1B:
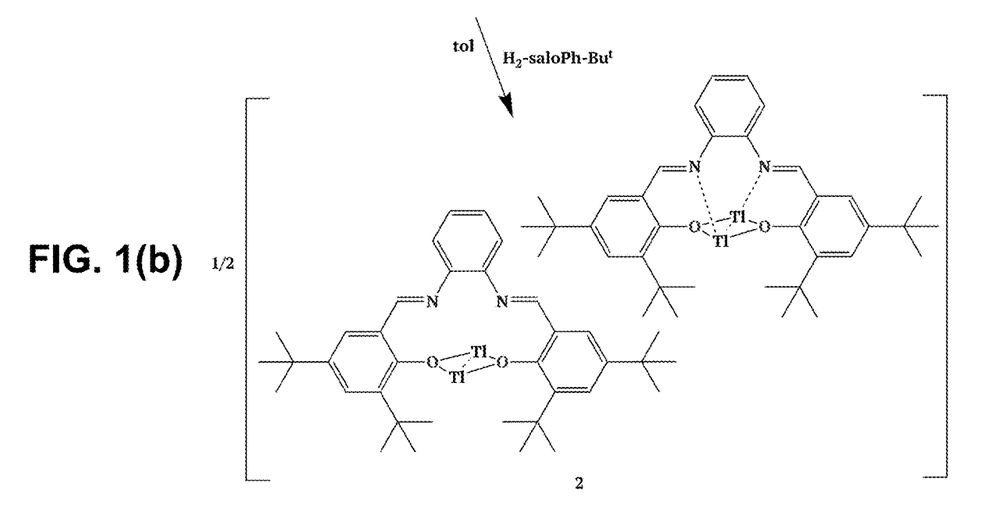

For these reactions, thallium ethoxide [Tl(OEt)] was reacted with N,N'-bis(3,5-di-t-butylsalicylidene)-ethylenediamine (H$_2$-salo-Bu$^t$) or N,N'-bis(3,5-di-t-butylsalicylidene)-1,2-phenylenediamine (H$_2$-saloPh-Bu$^t$). The products were identified by single crystal X-ray diffraction as: [((μ-O)$_{2,\kappa^1}$—(N)(N')salo-Bu$^t$)Tl$_2$], hereinafter referred to as compound 1, and {[((μ-O)$_2$saloPh-Bu$^t$)Tl$_2$][((μ-O)$_{2,\kappa^1}$—(N)(N')saloPh-Bu$^t$)Tl$_2$]}, hereinafter referred to as compound 2. FIG. 1(a) shows a schematic representation of the synthesis of compound 1. FIG. 1(b) shows a schematic representation of the synthesis of compound 2.

The synthesis of the exemplary Tl-salen compounds began with a 1:1 stoichiometry of [Tl(OEt)] and the appropriate H$_2$-saloR'—Bu$^t$. H$_2$-salo-Bu$^t$ or H$_2$-saloPh-Bu$^t$ were synthesized from the reaction of ethylenediamine with either 3,5-di-tert-butyl-2-hydroxybenzaldehyde or ortho-phenylenediamine, respectively. See C. Sohn et al., *Dalton Trans.* 45, 5825 (2016). Each precursor was individually dissolved in toluene and then the colorless Tl solution was slowly added to the bright yellow H$_2$-saloR'—Bu$^t$ solutions. The Tl/salo-Bu$^t$ reaction turned to a bright orange color, whereas the Tl/saloPh-Bu$^t$ mixture turned to a cherry red color. After stirring for 12 h, the cap was removed to allow for the volatile component to evaporate. X-ray quality crystals were isolated by slow evaporation and solved as the [Tl$_2$(saloR'—Bu$^t$)] complexes 1 and 2. A rational synthesis was undertaken using a 2:1 [Tl(OEt)]:H$_2$-saloR'—Bu$^t$ ratio. The same products were isolated but lacked the residual H$_2$-saloR'—Bu$^t$ impurity associated with the original 1:1 stoichiometry. Therefore, the following experimental data are for the rational synthesis 2:1 stoichiometry route.

Structure

Figure 2:
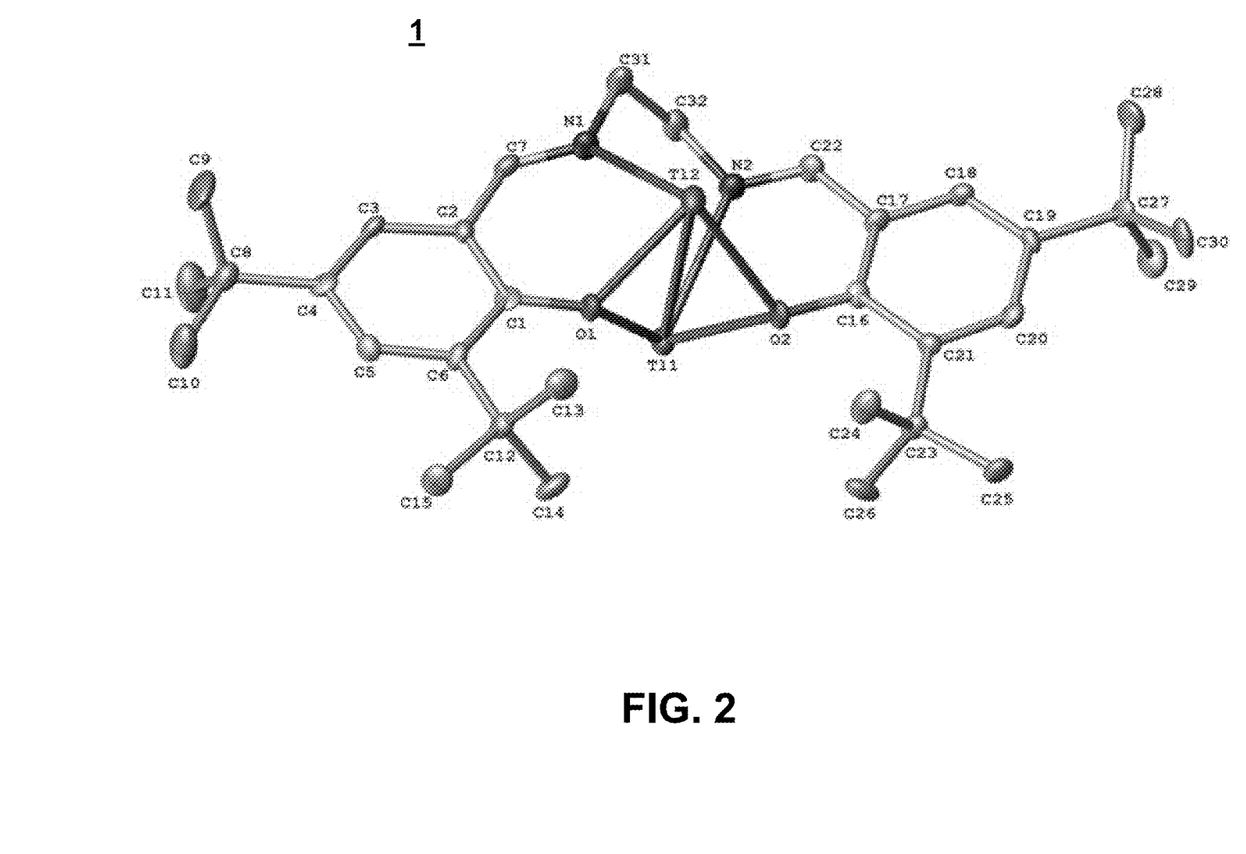
FIG. 2 is a structure plot of compound 1 [((μ-O)$_{2,\kappa^1}$—(N)(N')salo-Bu$^t$)Tl$_2$]. Thermal ellipsoids of the heavy atoms are represented at the 30% level. Carbon atoms are shown as ball and stick for clarity.
Figure 3A:
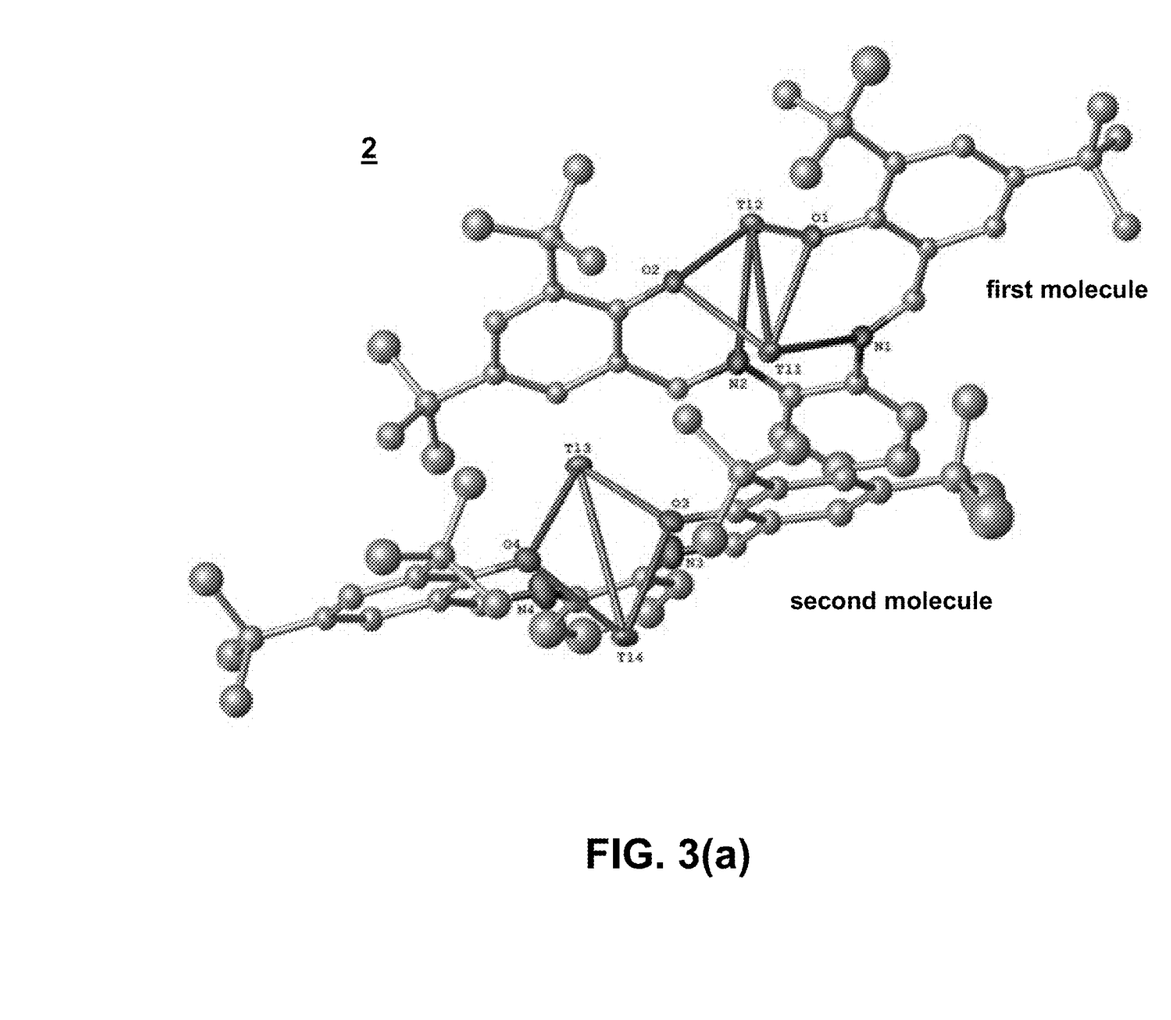
FIG. 3(a) is a structure plot of compound 2 {[((μ-O)$_2$saloPh-Bu$^t$)Tl$_2$][((μ-O)$_{2,\kappa^1}$—(N)(N')saloPh-Bu$^t$)Tl$_2$]}. Thermal ellipsoids of the heavy atoms are represented at the 30% level. Carbon atoms are shown as ball and stick for clarity. There are two molecules in the unit cell.
Figure 3B:
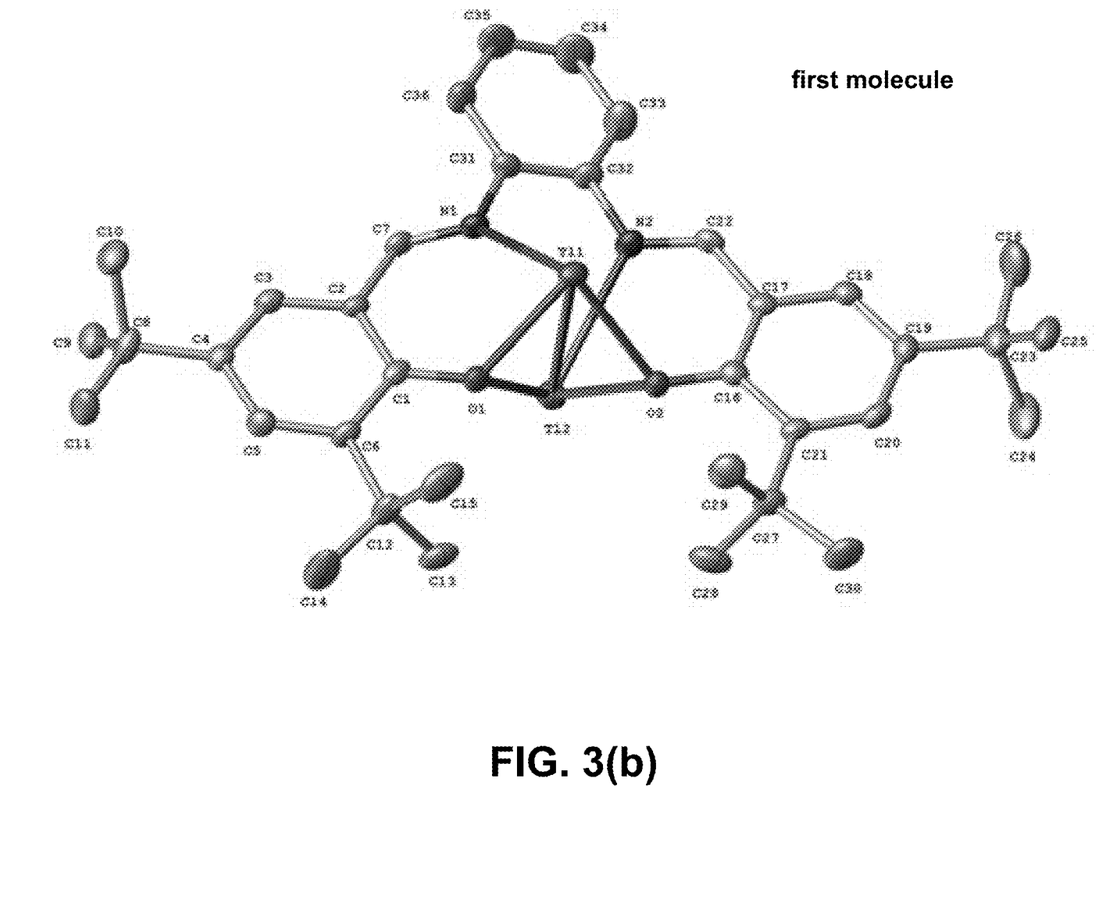
FIG. 3(b) is an individual structure plot of molecule 1 from compound 2.
Figure 3C:
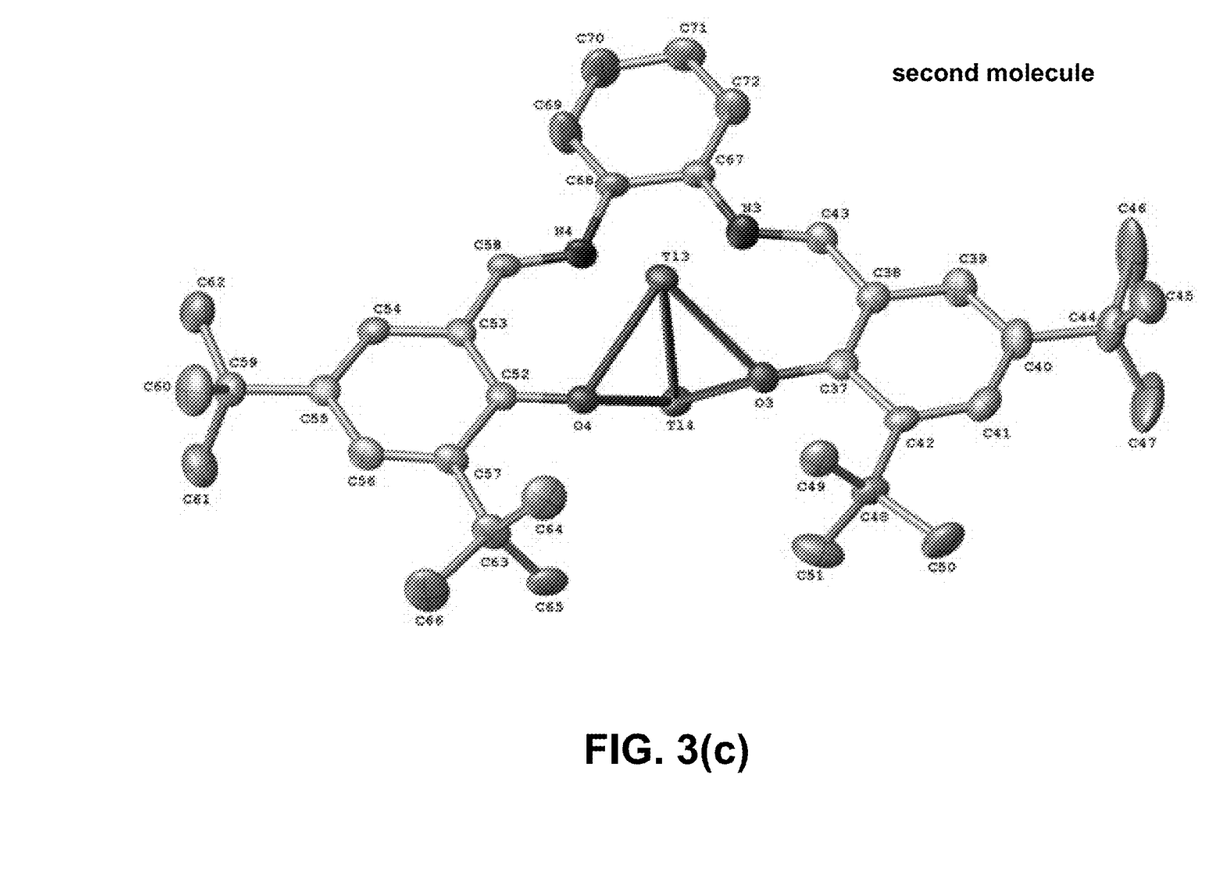
FIG. 3(c) is an individual structure plot of molecule 2 from compound 2.

Single crystal X-ray structure experiments were undertaken with the isolated crystals. Data collection parameters from the single crystal x-ray diffraction analysis are listed in Table 1. Table 2 lists select averaged metrical data solved for compounds 1 and 2. FIG. 2 is a structure plot of the dinuclear compound 1. FIG. 3(a) is a structure plot of the dinuclear compound 2. For both complexes, a single salen ligand was found to coordinate two Tl(I) atoms. For 1, the Tl metal centers are bridged by the two O atoms of the salen and complete their distorted trigonal pyramidal (TP) coordination by binding to a different N atom. The structure of 1 is also shown schematically in FIG. 1(a). The crystal structure of 2 yields two molecules in the unit cell that have two different structural motifs, which are drawn in FIGS. 3(a) and 1(b). The first molecule is similar to compound 1, forming the pseudo-TP coordination through the use of both O atoms and one N atom per metal center, as shown in FIG. 3(b); however, the Tl---N interaction of this molecule of compound 2 is significantly reduced compared to compound 1. The second molecule in the unit cell has no Tl---N coordination, producing a 'butterfly' arrangement, as shown in FIG. 3(c). Additionally, for both 1 and 2, the two Tl metal atoms within each molecule were found to be in close proximity to each other (Tl•••Tl=3.668 Å for 1 and 3.608 Å for 2) forming a weak Tl•••Tl interaction. The Tl atoms further complete their coordination sphere by interacting with the π-ring of the aryl moiety from another molecule (av 3.40 Å for 1 and 3.24 Å for 2).

The difference in Tl coordination/bonding is attributed to the different backbones of the salen ligand, where 1 possesses a more flexible ethylene linkage and 2 uses the rigid phenylene moiety. This leads to a much larger twist in the ring with a torsional angle of 129.9° between Tl(1)•••Tl(2) and C(31)-C(32) for 1 and 94.9° for Tl(1)•••Tl(2) and C(31)-C(32) or 81.3° for Tl(3)•••Tl(4) and C(67)-C(68) for the two molecules in the unit cell of 2. Further, there is a greater than 137° torsional angle between N(2)-C(32) and C(31)-N(1) for 1 but a much smaller angle noted for the two molecules of 2 [0.76° for N(4)-C(68)---C(67)-N(3); 0.46° for N(2)-C(32)---C(310-N(1)]. The Tl---N interactions shown as bonds for 1 are more than 0.2 Å shorter than the closest interactions recorded for 2. Due to additional electron density from the N atoms of the saloPh-Bu$^t$ ligand, the Tl•••Tl interaction is slightly greater for 2 (av 3.61 Å) versus 1 (3.67 Å) but both are well within the literature structure range of Tl•••Tl compounds (range 2.73-3.93 Å). See K. Akhbari and A. Morsali, *J. Mol. Struct.*, 878, 65 (2008); J. Beck and J. Strahle, *Z. Naturforsch. B: Chem. Sci.* 41, 1381 (1986); W. M. Boesveld et al., *Angew. Chem., Int. Ed.* 39, 222 (2000); M. V. Childress et al., *Inorg. Chem.* 45, 3864 (2006); G. B. Deacon et al., *J. Chem. Soc., Dalton Trans.*, 745 (2000); M. E. Desat et al., *Chem. Commun.* 53, 1510 (2017); E. J. Fernandez et al., *Inorg. Chim. Acta* 358, 4293 (2015); E. J. Fernandez et al., *J. Am. Chem. Soc.* 124, 5942 (2002); E. J. Fernandez et al., *Inorg. Chem.* 44, 6012 (2005); K. W. Hellmann et al., *Chem.—Eur. J.* 3, 1801 (1997); K. W. Hellmann et al., *Chem. Commun.*, 2515 (1996); K. W. Hellmann et al., *Angew. Chem., Int. Ed.* 36, 160 (1997); S. Henkel et al., *Angew. Chem., Int. Ed.* 33, 681 (1994); C. Jones and A. Stasch, *Main Group Met. Chem.* 29, 335 (2006); G. Ma et al., *Chem. Commun.* 46, 5370 (2010); D. R. Manke and D. G. Nocera, *Polyhedron* 25, 493 (2006); A. V. Protchenko et al., *Nature Chem.* 6, 315 (2014); A. L. Rheingold et al., *Chem. Commun.*, 1691 (1997); M. Schollenberger et al., *J. Organomet. Chem.* 460, 55 (1993); K. H. Stone et al., *Acta Crystallogr.*, Sect. B: *Struct. Sci.* 67, 409 (2011); W. Uhl et al., *Angew. Chem., Int. Ed.* 36, 64 (1997); M. Veith et al., *Chem. Ber.* 126, 2625 (1993); N. Wiberg et al., *Angew. Chem., Int. Ed.* 35, 65 (1996); N. Wiberg et al., *Eur. J. Inorg. Chem.*, 341 (2002); N. Wiberg et al., *Angew. Chem., Int. Ed.* 40, 1232 (2001); R. J. Wright et al., *J. Am. Chem. Soc.* 127, 4794 (2005); and M. S. Hill et al., *Chem. Commun.*, 3720 (2006). The Tl—O bond distances are nearly identical for both compounds. All remaining metrical data concerning the saloR'—Bu$^t$ are in agreement with each other. Literature metrical data comparisons for these compounds are difficult as these are the first structurally identified Tl-salen derivatives reported. Attempts to utilize the alkali metal salen derivatives as model systems do not work well as these tend to support clusters and not be individual metals. See S. C. Ball et al., *J. Chem. Soc.—Chem. Commun.*, 2147 (1995); I. Correia et al., *Eur. J. Inorg. Chem.*, 732 (2005); G. B. Deacon et al., *Inorg. Chim. Acta* 360, 1364 (2007); R. Jia rt al., *Aust. J. Chem.* 69, 20 (2016); and E. Solari et al., *J. Chem. Soc., Dalton Trans.*, 2471 (1991). In addition, other metal(I) compounds tend to be part of a salt structure.

Molecular modeling was undertaken to assist in understanding the structural properties noted for 1 and 2. The optimized DFT calculated structures were compared to the experimentally derived structures listed in Table 2. While the DFT models are of high quality, especially for the organic component of 1 and 2, there does appear to be a variation in the observed and calculated Tl•••Tl interactions. The overestimation of the model's Tl•••Tl interatomic distance by ~0.5% is believed to be due to a slight extension of the Tl—N bonds. NBO analysis confirmed that the shorter Tl•••Tl distance of 2 is based on a stronger Tl•••Tl stabilization energy (E) from the interaction of the Tl core (CR), Rydberg (RY*), or lone pair (LP) electrons, which leads to delocalization: 1, E=1112 kcal/mol; 2, E=140.23 kcal/mol. Additionally, a much stronger Tl---O interaction from CR—RY* interactions was noted for 1 (~160.36 kcal/mol) than for 2 (~92.34 kcal/mol). The stronger stabilization energy manifests as a decreased Tl—O distance in 1, as listed in Table 3.

Bulk Powder Characterization

The isolated crystals were dried and standard C, H, and N elemental analyses were undertaken for compounds 1 and 2. The final values were found to be in excellent agreement with the calculated experimental values, indicating the bulk powders are consistent with the solid-state structures.

Further characterization was undertaken using FT-IR spectroscopy. The loss of the —OH stretch around 3400 cm$^{-1}$ proved to be a viable means of tracking the progress of the reaction. In addition to the loss of this peak for the spectra of 1 and 2 versus the H$_2$-salo-Bu$^t$ and H$_2$-saloPh-Bu$^t$, little other differences were noted in the frequency and intensity of the various bends and stretches observed. One exception was the imine stretches of the free ligands which decreased in intensity and shifted upon complexation: H$_2$-salo-Bu$^t$ (1629 cm$^{-1}$); 1 (1595 cm$^{-1}$) and H$_2$-saloPh-Bu$^t$ (1636 cm$^{-1}$); 2 (1610 cm$^{-1}$). Previously, this was effectively used as a handle to identify the various Mg and Ca salen compounds. See T. J. Boyle et al., *Inorg. Chem.* 57(5), 2402 (2018). No other significant variations were observed. The Tl•••Tl interaction could not be established with this analysis.

Figure 4A:
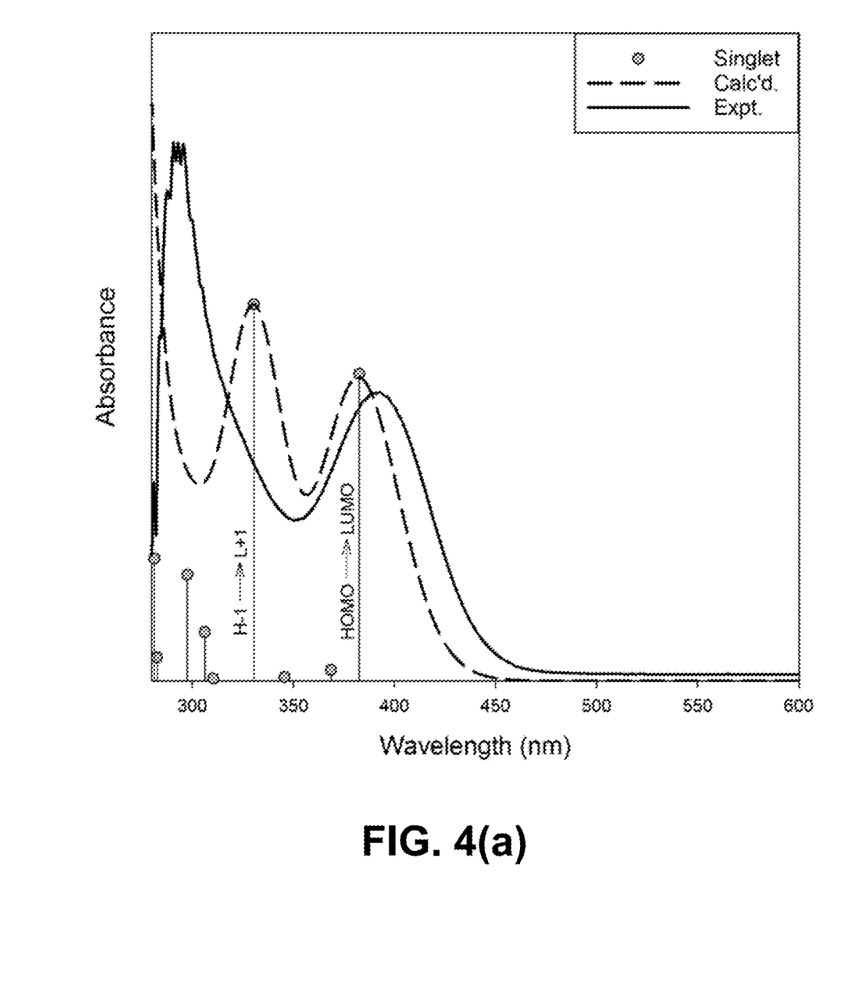
FIG. 4(a) is a UV-vis absorbance spectrum of compound 1 and comparison with calc'd spectrum.
Figure 4B:
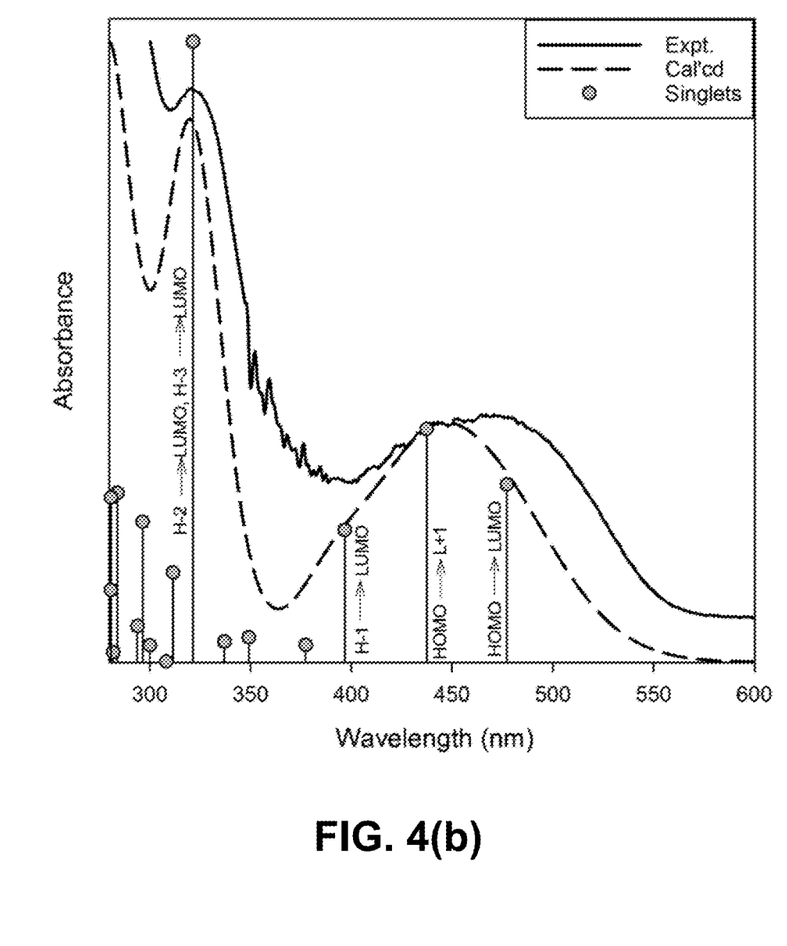
FIG. 4(b) is a UV-vis absorbance spectrum of compound 2 and comparison with calc'd spectrum. Selected electronic transitions are labeled.

Due to the intense color of the compounds, UV-vis absorbance spectral data were collected, as shown in FIGS. 4(a) and 4(b). The $\lambda_{max}$ noted for the π→π* at 344 nm for H$_2$-salo-Bu$^t$, and 347 nm for H$_2$-saloPh-Bu$^t$, were blue shifted to 295 and 323 nm upon complexation to the Tl metals. For 1, this may be a reflection of the lone pair of the N atoms interacting with the Tl metal centers which disrupts the planarity of the salen ligand. The N---Tl interaction is not as extensive for 2, which may explain the reduced shifts. In addition, broad absorptions associated with the Tl complexation were noted at 390 and 470 nm for 1 and 2, respectively. These appear to be the n-π* transitions of the salen ligands, possibly shifted due to the Tl interaction with the lone pair on the N atoms. As noted previously for the structure and model calculations, the Tl---N interactions are significantly stronger in 1 than 2, which is revealed in the intensity of the absorption. The d-d transitions were not noted for these Tl(I) complexes as the d-shell is full.

To complement the experimental data, time dependent density functional theory (TD-DFT) calculations with the LANL2DZ basis set for the Tl atoms were performed to calculate the computational UV-vis spectra. See M. M. Francl et al., *J. Chem. Phys.* 77, 3654 (1982); F. Furche and R. Ahlrichs, *J. Chem. Phys.* 117, 7433 (2002); and R. E. Stratmann et al., *J. Chem. Phys.* 109, 8218 (1998). After the initial structural relaxations, TD-DFT calculations were used to identify the energies of the 50 lowest-energy electronic transitions from the singlet states. The UV-vis absorbance spectra were then predicted from the calculated electronic transition in the 200-880 nm portion of the spectra using the GaussSum program. See N. M. O'Boyle et al., *J. Comp. Chem.* 29, 839 (2008). Plotted individual intensities and the Gaussian interpolations with a full-width-half-max (FWHM) value of 3000 cm$^{-1}$ are included in FIGS. 4(a) and 4(b). Singlet states as well as the calculated spectra are plotted and the intensities were scaled.

The two primary peaks in the experimental UV-vis absorbance spectral data for 1 occur at ~290 nm and ~394 nm. The calculated UV-vis spectrum contains a HOMO to LUMO transition for the ~390 nm peak. The calculated UV-vis absorbance spectra data for 2 includes a shoulder at ~322 nm (expt. 320 nm) and a second peak at ~450 nm (expt. 460 nm). The shoulder at ~310 nm is from HOMO-1 to LUMO and the HOMO to LUMO/LUMO+1 transitions in the singlet state. The addition of the phenylene moiety in 2 results in a red shift in the HOMO to LUMO, HOMO-1 to LUMO, and HOMO to LUMO+1 transition, which occurs in the experimental data. Based on these results, the UV-vis absorbance spectra of both 1 and 2 match well with experiment and reflect the changes in the structure of the compounds.

Solution-State NMR Analysis

To understand the solution behavior of these Tl-salen derivatives, multinuclear NMR spectra were collected using $^1$H, $^{13}$C, and $^{205}$Tl nuclei, the latter as shown in FIGS. 5(a), 5(b), 6(a) and 6(b). In CDCl$_3$, the $^1$H NMR spectra of 1 and 2 were found to be straightforward, with singlets noted in each spectrum for the t-butyl and the imine protons along with the expected aromatic doublets due to $^1$H J coupling on the rings. For 1, the methylene protons were clearly present at 3.22 ppm; whereas, for 2, the four aromatic peaks of the saloPh-Bu$^t$ backbone were present with some $^1$H J coupling observed. Based on the simplistic spectrum reported, there must be some dynamic equilibration present that equates the two, unique structures noted in the solid state of 2. This is easily envisioned through a change in the coordination of the Tl---N environments.

The $^{13}$C NMR spectra of 1 and 2 were dominated by the number of aromatic peaks; however, the imine carbon resonance was observed at δ 164.7 and 166.5 ppm for 1 and 2, respectively. The slight shift observed may reflect the different heteroatoms the Tl atoms appear to interact with in the solid state. The methylene carbons were noted only for 1 at δ 62.4 ppm. Two quaternary methyl resonances were observed for the tert-butyl of the phenoxide moiety but only one methyl resonances. The simplistic $^{13}$C NMR spectrum noted for 1 is consistent with the observed solid-state structure but for 2 the spectrum suggests a change in the bonding modes of the two molecules; however, conclusive statements with respect to the Tl•••Tl interaction required additional NMR experiments.

The activity of a series of thallium aryloxides [Tl(OAr)] compounds has been studied and it was found that the increase in covalency results in a downfield chemical shift of the $^{203,205}$Tl resonances. See C. A. Zehmann et al., *Inorg. Chem.* 40, 2177 (2001). It was of interest to determine the solution behavior of 1 and 2 (i.e., structure retention, dynamic behavior for the Tl•••Tl interaction, etc.). The $^{205}$Tl spectra are expected to be complex since both nuclei possess a spin I=½ with high natural abundance 29.5% ($^{203}$Tl) and 70.5% ($^{205}$Tl) and high relative sensitivity 0.18 and 0.19 (versus $^1$H=1.00), respectively. However, these properties allow the generation of useful spectral information at relatively low concentrations due to its sensitivity to very small changes in the local bonding environment. In addition, $^{203,205}$Tl isotopes should allow for identification of the Tl•••Tl through bond J coupling that will occur for 1 and 2, if they maintain their structures in solution.

Figure 5A:
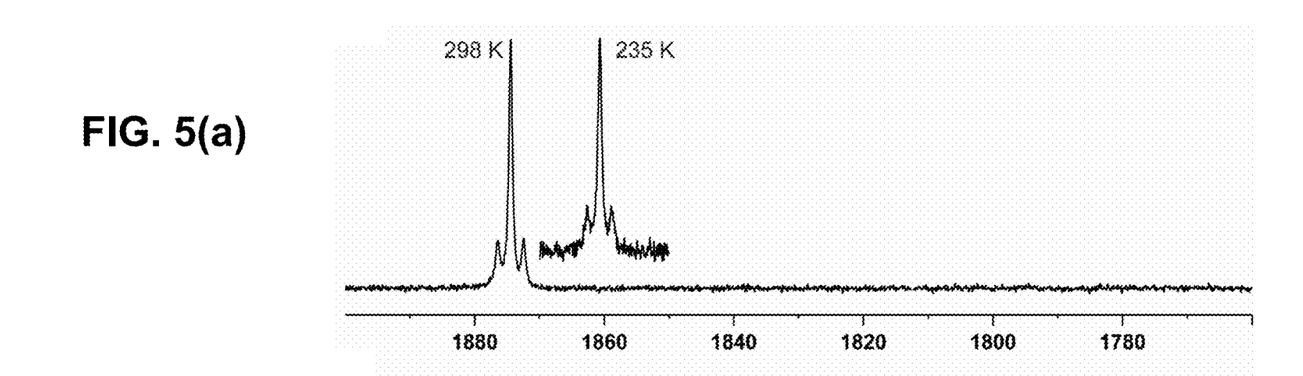
FIG. 5(a) is a solution $^{205}$Tl NMR of compound 1 at 298 K and 235 K (inset).
Figure 5B:
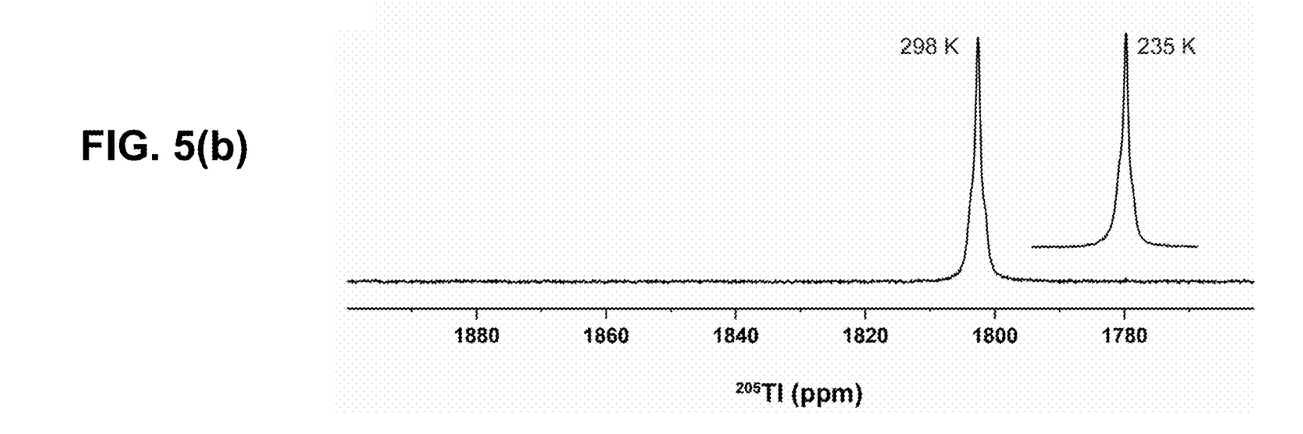
FIG. 5(b) is a solution $^{205}$Tl NMR of compound 2 at 298 K and 235 K (inset)
Figure 6A:
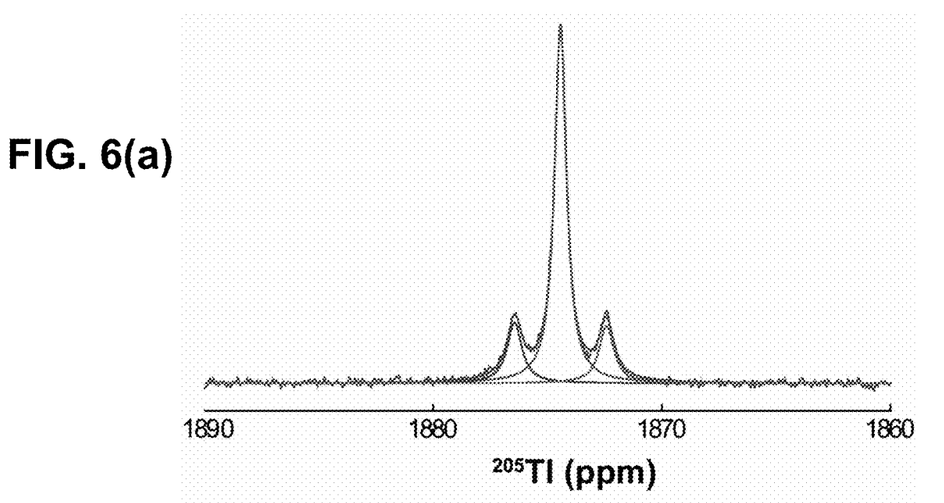
FIGS. 6(a) and 6(b) are simulations of the $^{205}$Tl NMR showing the doublet consistent with a 2 Tl center cluster with $^{203}$Tl-$^{205}$Tl J coupling and the center singlet for $^{205}$Tl bonded to $^{205}$Tl in compounds 1 and 2, respectively.
Figure 6B:
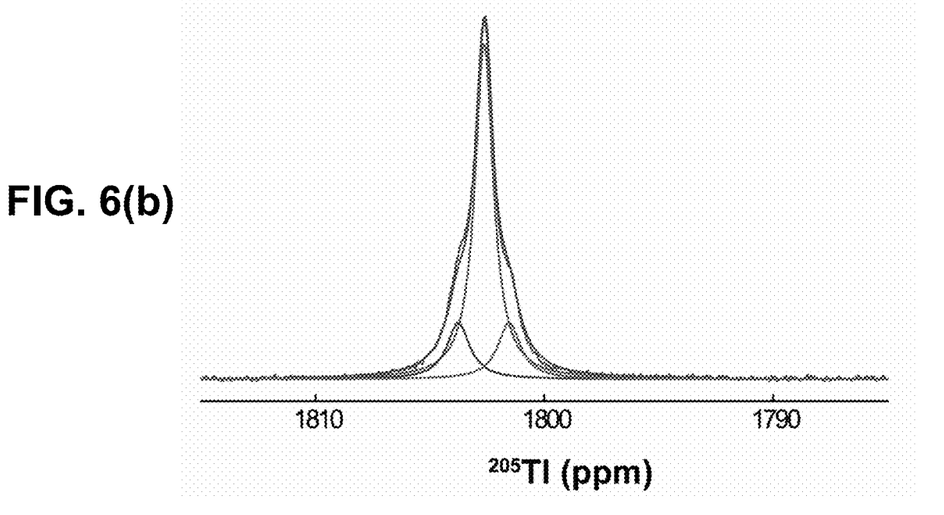

For both 1 and 2, the room temperature $^{205}$Tl NMR spectrum, shown in FIGS. 5(a) and 5(b), respectively, revealed a broad singlet with a minor overlapping doublet at δ 1874 ppm (J($^{203}$Tl-$^{205}$Tl)=1.16 kHz) and 1803 ppm (J($^{203}$Tl-$^{205}$Tl)=0.64 kHz), respectively. These $^{205}$Tl NMR shifts are consistent with close interacting Tl cations noted in a series of varied [Tl(OAr)]$_n$ and shifted from the mixed metal [Tl$_2$Cu(OAr)$_4$] and [TlTi(OAr)$_5$] compounds. See C. A. Zehmann et al., *Inorg. Chem.* 40, 2177 (2001); M. V. Childress et al., *Inorg. Chem.* 45, 3864 (2006); and T. J. Boyle et al., *Inorg. Chem.* 41, 946 (2002).

Further analysis of these peaks confirmed that the overlapping doublet is due to the $^{203}$Tl-$^{205}$Tl J-coupling, as shown in FIGS. 5(a) and 5(b). The dominant singlet arises from a $^{205}$Tl nuclei located near another $^{205}$Tl nuclei (70.5%), which will have the same chemical shifts (equivalent bonding environments) and thus no Tl—Tl J-coupling will be observed. These NMR spectra confirm that in solution the two Tl environments are equivalent for both 1 and 2. This, in agreement with the other NMR data, suggests that the two structures noted for the single crystal X-ray structure of 2, must undergo a dynamic process (ligand fluctuations) in solution to equate the Tl environments. The doublet arises from a $^{205}$Tl nuclei that is J-coupled to a neighboring $^{203}$Tl, with the integrated intensities of the doublet matching the 29.5% relative abundance of the $^{203}$Tl isotope. The observed doublet and relative intensities noted for 1 and 2, shown in FIGS. 6(a) and 6(b), confirms that two Tl atoms are present and close to each other. Further, the lack of higher order multiplets in the $^{205}$Tl NMR spectra, directly indicates that additional Tl•••Tl interactions or clusters are not present. This Tl-Tl J coupling is consistent with the $^{205}$Tl NMR data obtained on [Tl(OAr)]$_n$ complexes previously reported. See C. A. Zehmann et al., *Inorg. Chem.* 40, 2177 (2001). Variable temperature $^{205}$Tl NMR was also obtained down to 235 K (see inset of FIGS. 5(a) and 5(b)). At this temperature, the peaks shift for 1 and 2 to 1861 and 1780 ppm, respectively, however, no additional dynamic processes are resolved at this reduced temperature. This is in contrast to the very dynamic behavior observed for the reported [Tl(OAr)] compounds, where dynamic spectral averaging was easily observed for tempertures below room temperature, with the increased stability attributed to the chelating nature of the salen ligand. See C. A. Zehmann et al., *Inorg. Chem.* 40, 2177 (2001).

Fluorescence Measurements

Since the absorption peaks of the n→p* transitions of the salen ligands, noted in the UV-vis absorbance spectra (see FIGS. 4(a) and 4(b)), overlap with a common, handheld 405-nm-laser diode pointer, illumination by this source provides a simple, practical way to enable measurement of the fluorescent properties of these compounds. Upon illumination, the powder of 1 was visibly very bright yellow color while compound 2 was a noticeably less intense red color. Quantification of the fluorescence output revealed that for an almost identical setup, 1 was roughly 15 times brighter than 2, based on peak height.

Figure 7A:
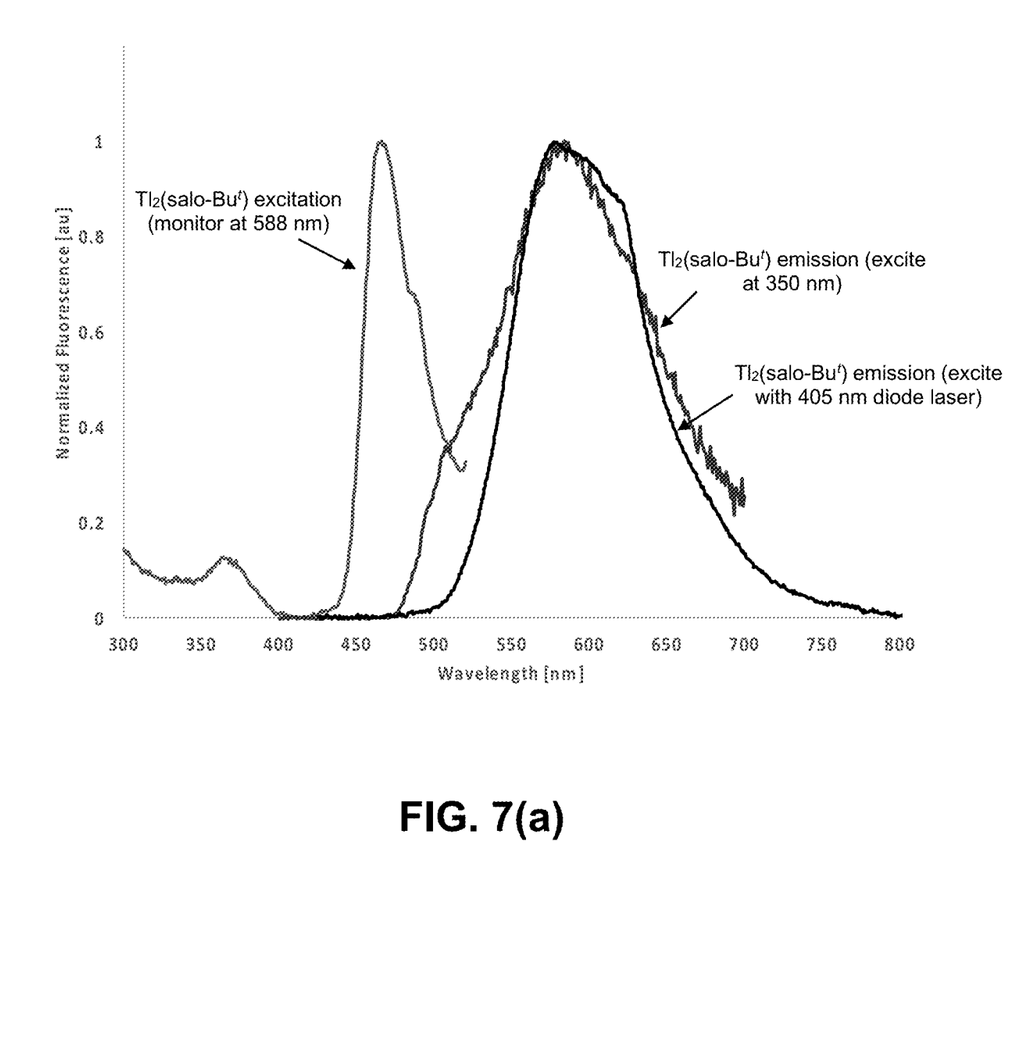
FIG. 7(a) shows room temperature emission data for compound 1.
Figure 7B:
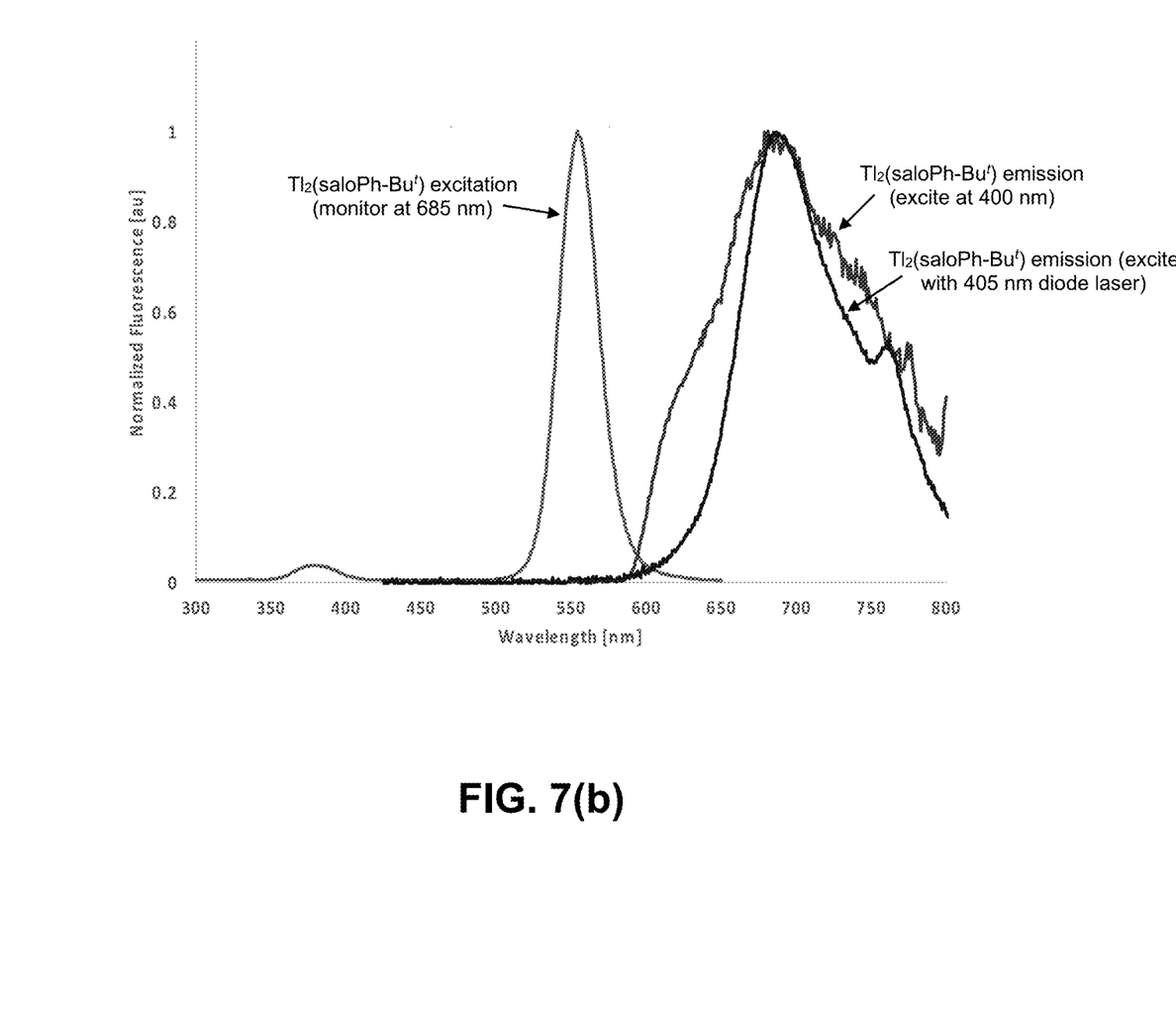
FIG. 7(b) shows room temperature emission data for compound 2. Excitation spectra were monitored at 588 and 685 nm, respectively. Emission spectra were excited at 350 and 400 nm, respectively; or excited by a 405 nm diode laser.

The emission and excitation spectra of the H$_2$-salo-Bu$^t$, H$_2$-saloPh-Bu$^t$, 1, and 2 when dissolved in toluene were collected over the 300-800 nm range for the H$_2$-salen, shown in FIGS. 7(a) and 7(b), to garner additional insight into their optical behavior. The excitation spectra recorded for the thallium derivatives peak at 360 and 380 nm for 1 and 2, respectively, that are not present in the same spectra of the free ligands. Therefore, these absorbances were attributed to the Tl•••Tl metal centers. Interestingly, the emission profiles of 1 and 2 in toluene are nearly identical in shape but the λ$_{max}$ of 2 is shifted to longer wavelengths by 105 nm (the local field energy is shifted by 2600 cm$^{-1}$ or 0.33 eV). When 1 or 2 are excited with a handheld laser pointer, which would be useful for real-world field evaluations, the emission spectra are nearly identical to the single-mode diode laser.

Figure 8:
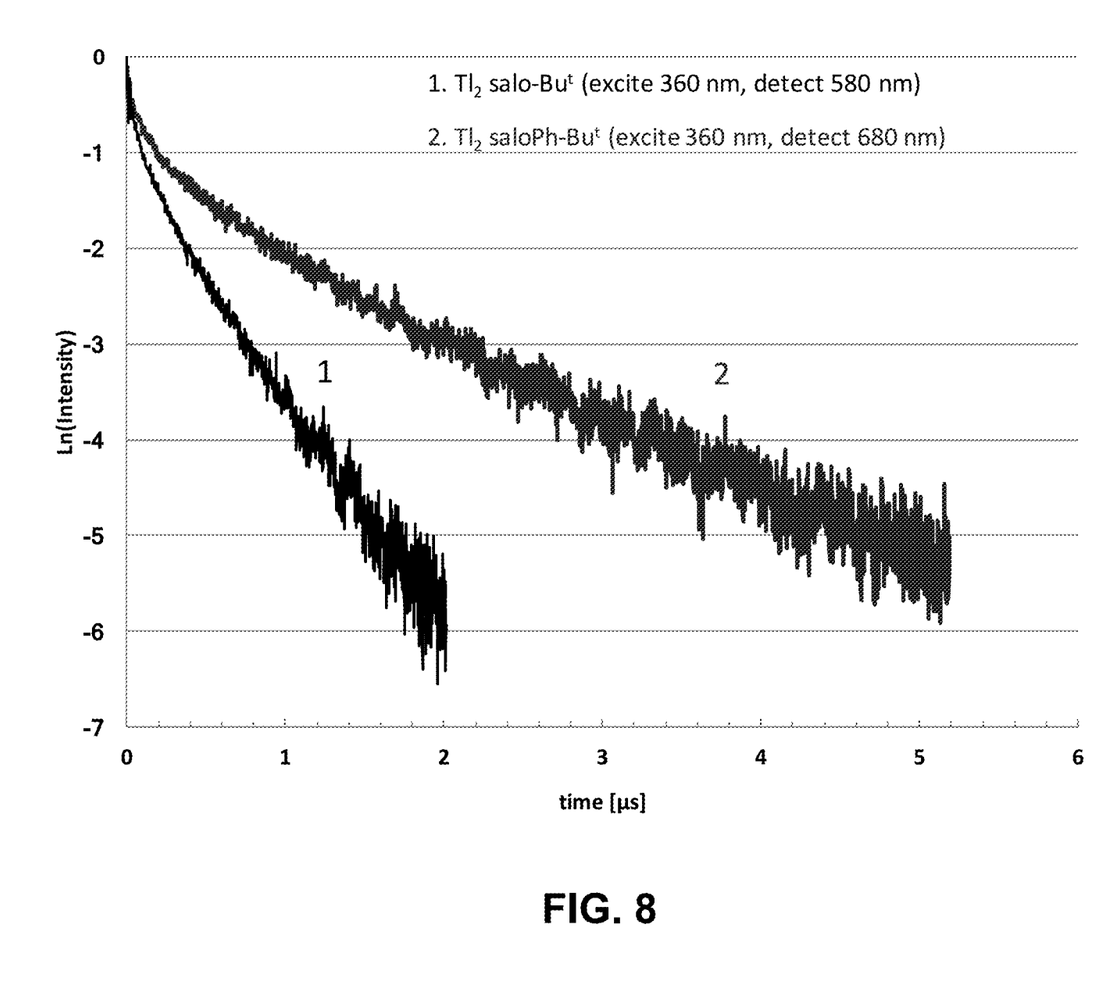
FIG. 8 is a graph of the time decay profile of the excitation (at 360 nm) from pulsed frequency-doubled OPO tuned to peak absorption for compound 1, detected at 580 nm, and compound 2, detected at 680 nm.

To examine the time behavior of the powders, a 6-ns pulsed, frequency-doubled optical parametric oscillator (OPO) was tuned across the excitation peaks for the Tl$_2$ complexes in toluene. The spectral profiles for both 1 and 2 were identical and the relative intensities were similar to those obtained when exciting with the cw sources. FIG. 8 shows the time decay profiles of the fluorescence for 1 and 2, respectively, from the pulsed excitation source tuned to 360 nm. Both compounds exhibit non-exponential decays as is expected for concentrated molecular crystals. At long times, the decay of 1 slows to a somewhat exponential decay value of ~0.4 μs, whereas 2 is even more exponential at long times with a value of ~1.4 μs. These values varied by less than 10% as the exciting wavelength was tuned across the excitation peak. It is of note that the intensity and time profiles of the powders remained unchanged after exposure to air for an extended period (<3 mo).

Tracer Properties

Attempts were made to screen these compounds as potential deep-underground tracer molecules, as these molecules might serve as tags themselves or as models for other Group 13 molecules. A number of the important characteristics that a tracer must display are stability to underground strata (i.e., cannot irreversibly bind to bedrock), stability to high temperatures and pressures, and resistance to ion exchange due to the potential toxicity of the Tl cation, if released. While the presence of toxic Tl may limit these compounds' practical utility, it is important to note that their high solubility and luminescent properties will allow for useful laboratory adsorption studies and model studies focused on other, less-toxic Group 13-salen complexes. In particular, the high luminosity of 1 and 2 will allow for facile rock formation absorption studies using visual inspections versus physically analyzing strata or other more time-consuming approaches, particularly in laboratory or pilot-scaled testing studies. Preliminarily screening experiments to evaluate 1 and 2 were undertaken and the results are described below.

A simple column was investigated to determine if these compounds could pass through a sand environment without adsorbing irreversibly or 'sticking'. More complex columns are necessary to draw definitive answers about the elution of these compounds but as a preliminary evaluation, silica (i.e., sand) was selected as a useful starting point due to its ubiquity in underground wells. A column was packed with sand, wetted with toluene, and then the precursor dissolved in toluene was added to the column and allowed to gravity drain. Additional toluene was added to the column and the effluent was collected, dried in vacuo, and weighed. For compound 1, the sample readily passed through the column with complete recovery of the taggant. In contrast, compound 2 had nearly half of the sample adsorb irreversibly on this simple column. It is unclear as to what the difference is in the retention of these compounds but based on the structural analyses and the computational models, the complexation of the Tl metals must be a contributing factor. As noted previously, the majority of the bond distances are longer for 1 than for 2, but the metals in 1 possess the additional Tl---N interaction, which may lend more chemical stability to the overall structure. This assumption was evaluated using DFT calculations through natural bond orbital (NBO) analysis (Tables 3 and 4). For both 1 and 2 the Tl---N and Tl—O interactions were determined and found to be consistent with the experimentally derived metrical data. Compound 1 was calculated to have significantly stronger interactions with the N atoms than was observed for 2. Interestingly, compound 2 was found to have more Tl—O interactions than 1 but the over strength of these contacts was determined to be weaker than 1. Combined the DFT-NBO calculations and experimental results indicate that the increased coordination of 1 through the Tl---N interaction lends stability to the molecule.

Additional exploration of the properties of these compounds lends further credence to the stability of 1 over 2. Mimicking an underground 'oil' environment was undertaken by placing each complex individually into a Parr™ reactor in dodecane. These potential taggants must obviously be inert to any ion-exchange reactions underground in order to maintain structural integrity. Therefore, other potential ions commonly found underground were introduced as oxides or hydroxides to simulate the reservoir environment. The samples were sealed and were heated to 150° C. for 12 h. After this time, the soluble fraction was collected and dried. Based on FT-IR and UV-vis absorbance spectroscopic results, only compound 1 survived this experiment. The same study was repeated in toluene at 120° C. with identical results. As suggested by the crystal structure and DFT calculations, compound 1 appears to be much more chemically and thermally stable than 2, which is attributed to the additional Tl---N interaction noted for 1.

The present invention has been described as thallium salen fluorescent tracers. It will be understood that the above description is merely illustrative of the applications of the principles of the present invention, the scope of which is to be determined by the claims viewed in light of the specification. Other variants and modifications of the invention will be apparent to those of skill in the art.

TABLE 1

Data collection parameters for compounds 1 and 2.

| | Compound | |
|---|---|---|
| | 1 | 2 |
| Chem. Formula | $C_{32}H_{46}N_2O_2Tl_2$ | $C_{36}H_{46}N_2O_2Tl_2$ |
| Form. Weight | 899.45 | 947.49 |
| temp (K) | 100.(2) | 100.(2) |
| space group | orthorhombic P 21 21 21 | orthorhombic P b c a |
| a (Å) | 6.1980(2) | 17.7707(5) |
| b (Å) | 19.1223(6) | 25.4858(7) |
| c (Å) | 27.6952(8) | 31.6358(9) |
| V (Å$^3$) | 3282.44(18) | 14327.9(7) |
| Z | 4 | 16 |
| $D_{calc'd}$(Mg/m$^3$) | 1.820 | 1.757 |
| μ(Mo, Kα) (mm$^{-1}$) | 18.847 | 17.311 |
| R1$^a$ (%) (all data) | 2.70 (2.75) 6.77 | 2.82 (3.08) |
| wR2$^b$ (%) (all data) | (6.80) | 7.04 (7.19) |

$^a$R1 = Σ | |F$_o$|-|F$_c$| | / Σ |F$_o$| × 100
$^b$wR2 = [Σ w ( F$_o^2$ − F$_c^2$ )$^2$ / Σ (w |F$_o$|$^2$)$^2$]$^{1/2}$ × 100

TABLE 2

Select metrical data for compounds 1 and 2 and DFT calculated distances from equilibrium structure of 1 and 2.

| Compound | 1 (Expt) | 1 (Calc'd) | 2 (Expt) | 2 (Calc'd) |
|---|---|---|---|---|
| | Distances (Å) | | | |
| Tl ••• Tl | 3.67 | 3.689 | 3.61 | 3.634 |
| Tl-N | 2.67 | 2.714 | — | 2.791 |
| Tl-O | 2.51 | 2.477 | 2.51 | 2.545 |
| N—C—C—N | 1.45 | 1.441 | 1.42 | 1.401 |
| N—C—C—N | 1.54 | 1.536 | 1.40 | 1.416 |
| Tl—C$_6$H$_2$(Bu$^t$) (centroid) | 3.40 | 3.440 (0.509)* | 3.24 | 3.551 (0.058) |
| | Angles (deg) | | | |
| O—Tl—O | 74.49 | 74.884 | 72.06 | 72.214 |
| O—Tl—N | 67.91 | 65.794 | — | 61.780 |

TABLE 2-continued

Select metrical data for compounds 1 and 2 and DFT calculated distances from equilibrium structure of 1 and 2.

| Compound | 1 (Expt) | 1 (Calc'd) | 2 (Expt) | 2 (Calc'd) |
|---|---|---|---|---|
| O—Tl···Tl | 43.00 | 43.963 | 44.01 | 44.448 |
| N—Tl···Tl | 61.91 | 60.702 | — | 51.463 |

*From replicated molecular structure

TABLE 3

Donor-acceptor interactions for Tl atoms in compound 1 and their stabilization energies (E) from second order perturbation theory. The three largest stabilization energies for Tl-Tl, Tl-C, Tl-N, and Tl-O interactions are included.

| | Donor (i) | | Acceptor (j) | | E |
|---|---|---|---|---|---|
| Interaction | NBO | Atom | NBO | Atom | (kcal/mol) |
| Tl—Tl | RY* | Tl 1 | RY* | Tl 2 | 112.05 |
| | CR | Tl 1 | RY* | Tl 2 | 107.08 |
| | CR | Tl 1 | RY* | Tl 2 | 89.20 |
| Tl—C | CR | Tl 2 | RY* | C 75 | 108.06 |
| | CR | Tl 1 | RY* | C 78 | 105.73 |
| | CR | Tl 1 | RY* | C 58 | 103.51 |
| Tl—N | CR | Tl 2 | RY* | N 6 | 77.40 |
| | CR | Tl 1 | RY* | N 5 | 75.86 |
| | CR | Tl 2 | RY* | N 5 | 52.55 |
| Tl—O | CR | Tl 1 | RY* | O 4 | 160.36 |
| | CR | Tl 2 | RY* | O 3 | 159.36 |
| | CR | Tl 1 | RY* | O 3 | 108.06 |

TABLE 4

Donor-acceptor interactions for Tl atoms in compound 2 and their stabilization energies (E) from second order perturbation theory. The three largest stabilization energies for Tl-Tl, Tl-C, Tl-N, and Tl-O interactions are included.

| | Donor (i) | | Acceptor (j) | | E |
|---|---|---|---|---|---|
| Interaction | NBO | Atom | NBO | Atom | (kcal/mol) |
| Tl—Tl | CR | Tl 1 | RY* | Tl 2 | 140.23 |
| | LP | Tl 1 | RY* | Tl 2 | 98.49 |
| | CR | Tl 1 | RY* | Tl 2 | 81.03 |
| Tl—C | CR | Tl 1 | RY* | C 51 | 64.85 |
| | CR | Tl 2 | RY* | C 15 | 64.83 |
| | CR | Tl 1 | RY* | C 7 | 63.99 |
| Tl—N | CR | Tl 1 | RY* | N 5 | 144.02 |
| | CR | Tl 2 | RY* | N 6 | 143.91 |
| | CR | Tl 1 | RY* | N 5 | 140.35 |
| Tl—O | CR | Tl 1 | RY* | O 3 | 92.34 |
| | CR | Tl 2 | RY* | O 4 | 92.34 |
| | CR | Tl 1 | RY* | O 3 | 46.19 |

I claim:

1. A method to synthesize a thallium salen according to the reaction:

2[Tl(OR*)]+H$_2$-saloR'—R→[Tl$_2$(saloR'—R)]+ 2HOR* where Tl(OR*) is a thallium alkoxide, H$_2$-saloR'—R is a salen ligand, and Tl$_2$(saloR'—R) is the thallium salen.

2. The method of claim 1, wherein R is a substituent on a salen ring comprising a hydrocarbon, nitrate, sulfate, or alkoxide.

3. The method of claim 1, wherein R' is the linkage in the salen comprising an alkyl, phenyl, cyclohexyl, or hydrogen.

4. The method of claim 1, wherein H$_2$-saloR'—R is H$_2$-saloR'—Bu$^t$ and R' is CH$_2$CH$_2$ or C$_6$H$_4$.

5. A thallium salen having the chemical formula Tl$_2$(saloR'—R).

6. The thallium salen of claim 5, wherein R is a substituent on a salen ring comprising a hydrocarbon, nitrate, sulfate, or alkoxide.

7. The thallium salen of claim 5, wherein R' is the linkage in the salen comprising an alkyl, phenyl, cyclohexyl, or hydrogen.

8. The thallium salen of claim 7, wherein R' is CH$_2$CH$_2$ or C$_6$H$_4$.

9. The thallium salen of claim 5, wherein Tl$_2$(saloR'—R) is [((μ-O)$_{2,κ^1}$—(N)(N')salo-Bu$^t$)Tl$_2$] or {[((μ-O)$_2$saloPh-Bu$^t$)Tl$_2$][((μ-O)$_{2,κ^1}$—(N)(N')saloPh-Bu$^t$)Tl$_2$]}.

* * * * *